United States Patent [19]

Schwabe

[11] Patent Number: 5,296,224
[45] Date of Patent: Mar. 22, 1994

[54] KAVA-KAVA EXTRACT, PROCESS FOR THE PRODUCTION THEREOF AND USE THEREOF

[75] Inventor: Klaus-Peter Schwabe, Karlsruhe, Fed. Rep. of Germany

[73] Assignee: Dr. Wilmar Schwabe GmbH & Co., Fed. Rep. of Germany

[21] Appl. No.: 856,066
[22] PCT Filed: Sep. 5, 1991
[86] PCT No.: PCT/EP91/01687
§ 371 Date: May 7, 1992
§ 102(e) Date: May 7, 1992
[87] PCT Pub. No.: WO92/04036
PCT Pub. Date: Mar. 19, 1992

[30] Foreign Application Priority Data

Sep. 12, 1990 [DE] Fed. Rep. of Germany ....... 4028945

[51] Int. Cl.$^5$ ............................................. A61K 35/78
[52] U.S. Cl. ................................... 424/195.1; 514/456
[58] Field of Search ....................... 424/195.1; 514/456

[56] References Cited

FOREIGN PATENT DOCUMENTS 197806 6/1907 Fed. Rep. of Germany .
7893M 5/1970 France .
943121 11/1963 United Kingdom .

*Primary Examiner*—John W. Rollins
*Attorney, Agent, or Firm*—Frost & Jacobs

[57] ABSTRACT

Dry extract from kava-kava drug having a total content of kava lactones of at least 50% by weight and a flavokawin content of at the most 0.3% by weight. The extract is distinguished by good water solubility and high bioavailability after oral administration. To increase the kava lactone content in the extract and decrease the flavokawin content, a process is proposed in which the raw extract is brought into solution and the content of flavokawins diminished by cold precipitation or by solvent distribution, whereafter the solution is concentrated to dryness. Drugs are made using the dry extract.

13 Claims, 5 Drawing Sheets

KAVA-KAVA EXTRACT, PROCESS FOR THE PRODUCTION THEREOF AND USE THEREOF

The invention relates to an extract of low flavokawin content from the rhizome of *Piper methysticum Forst.* (pepper intoxicant, Piperaceae family) called "kava-kava", having a high content of kava lactones and good bioavailability.

In Polynesia, the home of the kava bush, since ancient times the natives have used an aqueous extract (cold macerate) of the drug for ritual and therapeutic purposes.

The relaxing action of the drug, which is used as phytotranquilizer for relaxing in cases of nervousness and overexcitement and as an agent for including sleep, is based on the occurrence of several 6-substituted 4-methoxypryones, that is the kava lactones kawain, dihydrokawain, methysticin, dihydromethysticin, yangonin and desmethoxyyangonin (cf. Hänsel et al., Deutsche Apothekerzeitung 125, No. 41, pages 2056–2058 (1985)). In addition, in the kava drug the yellow compounds flavokawin A and flavokawin B are contained to which skin-specific secondary effects are assigned (Shulgin, Bulletin on Narcotics, Vol. XXV, No. 2, pages 59–74 (1973)). Finally, the drug contains a series of further contents which have not yet been fully clarified and which are pharmacologically inert and referred to as "matrix substances".

Some kava lactones have also been synthesized, including kawain, the racemate being available commercially as psychopharmacological agent in the form of capsules containing 200 mg of the active agent.

The kava lactones are practically insoluble in water. For example, the maximum solubility of kawain at 21° C. is 2.2 mg/100 ml water. In the cold macerate used by the Polynesians, however, there is up to about 70 mg kava pyrones (total pyrone content) in every 100 ml macerate. It was concluded from this that the pharamacologically inert "matrix substances" contained in the drug act as solubilizers for the kava pyrones (cf. Hänsel et al., loc. cit.).

Because of its low bioavailability, the therapeutic effect obtainable with the kava lactone preparations hitherto on the market is unsatisfactory. The individual pure substances, irrespective of whether they are synthesized or isolated from the drug, must be administered in high doses because of their poor solubility whilst the dry extracts recovered from the drug have a total lactone content of only about 5 to 30% by weight so that in spite of the better solubility compared with the pure substances high doses must again be used to obtain the desired minimum titer in the blood or plasma.

The invention is therefore based on the problem of providing a dry extract having a substantially higher total lactone content but nevertheless good water solubility, with high bioavailability after oral administration and as low a flavokawin content as possible, as well as a simple process for the production thereof. The invention is further based on the problem of making pharmaceutical preparations with a high content of readily soluble and bioavailable kava lactones and as low as possible in flavokawin content, which can be administered orally and with which the danger of secondary effects due to discolouring of the skin is greatly reduced compared with the preparations known hitherto.

This problem is solved according to the invention by a dry extract from the rhizome of *Piper methysticum Forst.* which is characterized by a total content of kava lactones of at least 50% by weight and a flavokawin content of at the most 0.3% by weight. Preferably, the dry extract has a total content of kava lactones of 50 to 90% by weight and/or a flavokawin content of less than 0.3% by weight. An extract is particularly advantageous which has a total content of kava lactones of 60 to 80% by weight and the flavokawin content of which is less than 0.2% by weight.

Although the extract according to the invention is highly enriched compared with the extracts known hitherto and has a total content of kava lactones of up to 90% by weight and thus comes very close to the pure preparations, consisting for example of 100% kawain, it has surprisingly been found that the bioavailability of the extract according to the invention is substantially better, both compared to the dry extracts known hitherto and compared to the pure substances hitherto used as pharmaceutical preparations, although it has been possible to reduce the pharmacologically inert matrix content to 20% by weight whilst in the extracts known hitherto it was at least 70% by weight.

The dry extract according to the invention can therefore advantageously be employed for producing pharmaceutical preparations, in particular phytopharmaca, because to obtain the same pharmacological effect a smaller dosage than was necessary with the agents known hitherto is sufficient. As clinical tests have shown, the effective daily dose is about 300 mg of the extract according to the invention, corresponding to about 50 mg pure kawain, whilst the effective daily dose of kawain administered as pure substance is about 200 mg (cf. Kretschmer "Kavain als Psychopharmakon", MMW 4/1970, page 154–158).

The dry extract according to the invention can be prepared in simple manner in that the pulverized rhizome of *Piper methysticum Forst.* (rhizoma kava-kava) is extracted with a suitable solvent such as acetone, chloroform, ethyl acetate, low alkanols having 1 to 4 C atoms or at least 50% by weight mixtures thereof with water and the extract solution concentrated to dryness. The extraction can be carried out in the form of a percolation or a multistage agitating or vortex extraction at room temperature or at elevated temperature. Depending on the solvent used the raw extracts thus obtained have a content of kava lactones of about 50 to 70% by weight.

Thereafter, the raw extracts are again brought into solution and purified by cold precipitation from solvents miscible with water, in particular ethanol and acetone, or by solvent dispersion between an aqueous, aqueous-alcoholic or aqueous-acetonic first phase and a second phase not miscible with said first phase, the second phase being an organic phase formed from organic solvents such as chloroform, heptane, hexane, acetic acid ethyl ester and the like as well as mixtures thereof. The total content of kava lactones in the pure extracts thus obtained compared with the starting materials is only slightly reduced whilst the flavokawin content is drastically reduced to a third to a fifth of the starting content.

In the cold precipitation, as solvent firstly an organic solvent miscible with water is used, such as ethanol or another low alkanol or acetone, and the concentrated solution is mixed with water or with an alkanol-water mixture until a milky clouding occurs, thorough mixing being carried out, whereafter the mixture is cooled, preferably to 5° to 10°, and possibly allowed to stand for several hours, preferably about 12 to 24 hours. Thereafter the deposited precipitate is separated and the supernatant concentrated to dryness.

When using solvent dispersion the starting materials are either dissolved in an organic solvent not miscible with water, for example chloroform, hexane heptane or an acetic acid ethyl ester/hexane mixture, whereafter said organic phase is extracted in portions by shaking with small amounts of an aqueous, aqueous-alcoholic or aqueous-acetonic phase, for example water, ethanol/water or acetone/water. Alternatively, the starting materials are dissolved in an organic solvent miscible with water, for example ethanol or acetone, and the phase which is aqueous-alcoholic or aqueous-acetonic after addition of water is extracted several times by shaking or stirring with small amounts of an organic solvent not miscible with water.

In every case the kava lactones are in the aqueous, aqueous-alcoholic or aqueous-acetonic phase whilst the flavokawins concentrate in the organic phase immiscible with water and can be removed by separating said organic phase.

The pure extracts are of syrupy, oily or resinous consistency. For the manufacture of tablets, dragees or capsules they are mixed with usual auxiliary substances, for example finely dispersed silicic acid such as aerosil, and vacuum dried.

The invention will be explained in further detail with the aid of the following examples of embodiment. In the drawings:

EXAMPLE 1 a) Extraction with acetone 1 kg ground kava-kava drug is mixed with 5 times the amount by weight of acetone, homogenized and transferred to an extraction flask. Reflux extraction is carried out at 60° C. water bath temperature for 1 hour. After cooling the extract solution is filtered through a folded filter. The filtrate is concentrated to dryness (oily) in a rotary evaporator at 60° C. water bath temperature. The filtration residue may possibly be pressed out and extracted again.

The yield is 27.68 g oily extract with a 66% content of kava lactones.

b) Depletion of yellow dyes (flavokawins) by combination of solvent/cold precipitation 5 g of the kava extract obtained by the extraction described above is completely dissolved in 100 ml ethanol (96%) (A). Furthermore, 10 g of the kava extract is completely dissolved in 100 ml acetone (B).

20 ml of each of these starting solutions are diluted with water to 50 ml, a milky colouring occurring.

The aqueous dilutions are cooled for 12 hours to 5° to 10° C.

Thereafter, clarification is carried out by centrifugation or filtration and the kava lactones and flavokawins determined in the supernatant of the precipitation.

TABLE 1

| Starting content | | Content after solvent/cold precipitation |
|---|---|---|
| kava lactones | 100% | 93% (A) |
| flavokawins | 100% | 27% (A) |
| kava lactones | 100% | 87% (B) |
| flavokawins | 100% | 20% (B) |

Under these conditions a precipitation and depletion of the flavokawins to about 20% of the starting value takes place. The loss of kava lactones is about 10%.

EXAMPLE 2 a) Extraction with 95% ethanol 500 g ground kava-kava drug is mixed with 4000 g 95% ethanol, homogenized, transferred to an extraction flask and extracted for 1 hour at 60° C. water bath temperature. After cooling filtration is carried out through a suction filter. The drug residue is extracted again in the same manner and filtered. The extract solutions were combined and concentrated to dryness in a rotary evaporator at 60° water bath temperature.

Yield: 28.88 g kava extract with a 43% content of kava lactones.

b) Depletion of yellow dyes (flavokawins) by solvent distribution

Saturated solutions of the kava extract thus obtained are prepared in 30 ml of a mixture of 5 parts by volume acetic acid ethyl ester and 25 parts by volume n-hexane.

These batches are each extracted by shaking 3 times with 30 ml ethanol/water (ethanol content between 20 to 50% (v/v)).

In the ethanol/water phase or the hexane/acetic acid ester phase the amounts of kava lactones and flavokawins are determined by HPLC analysis.

Figure 1:
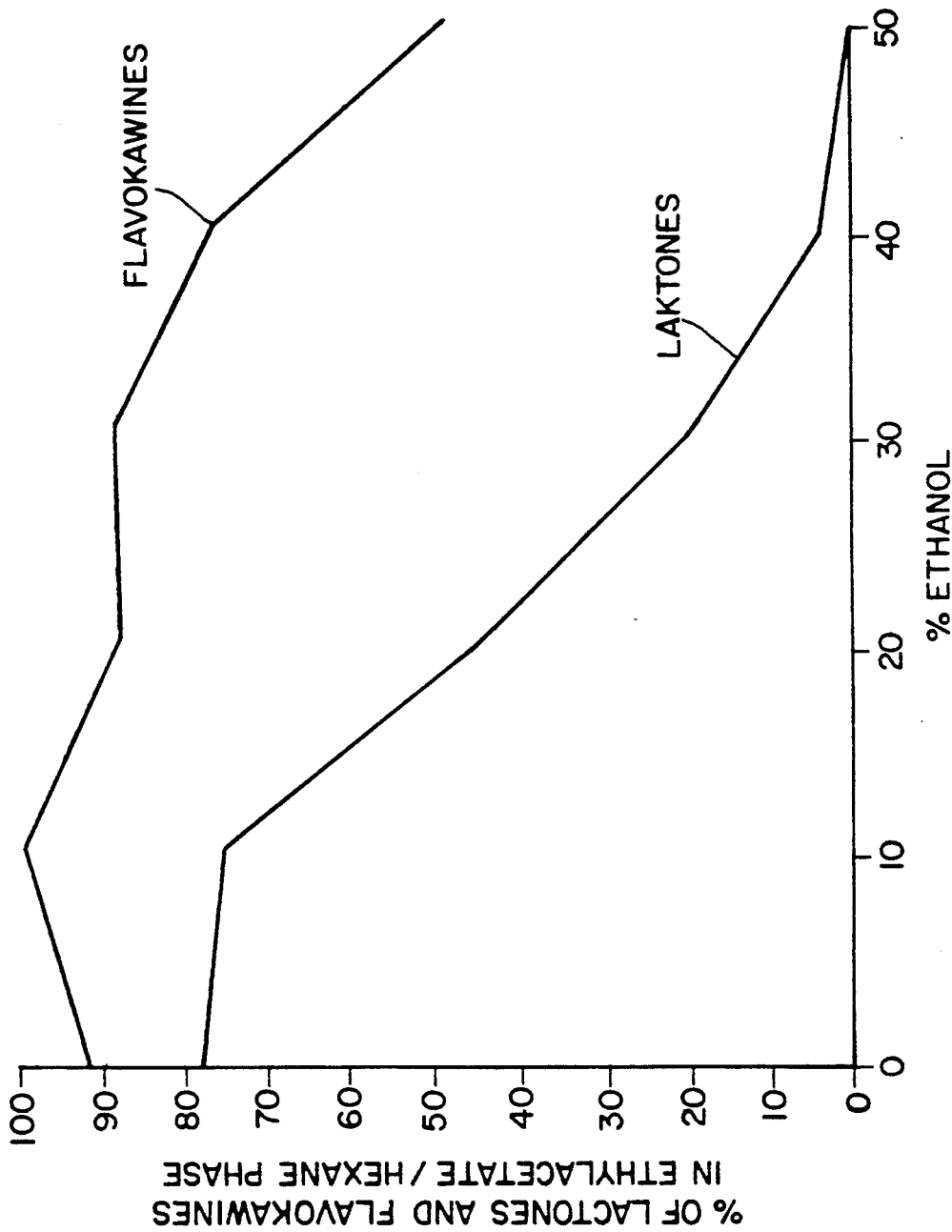
FIGS. 1 and 2 show substance distribution diagrams which will be explained in detail in conjunction with example 2.
Figure 2:
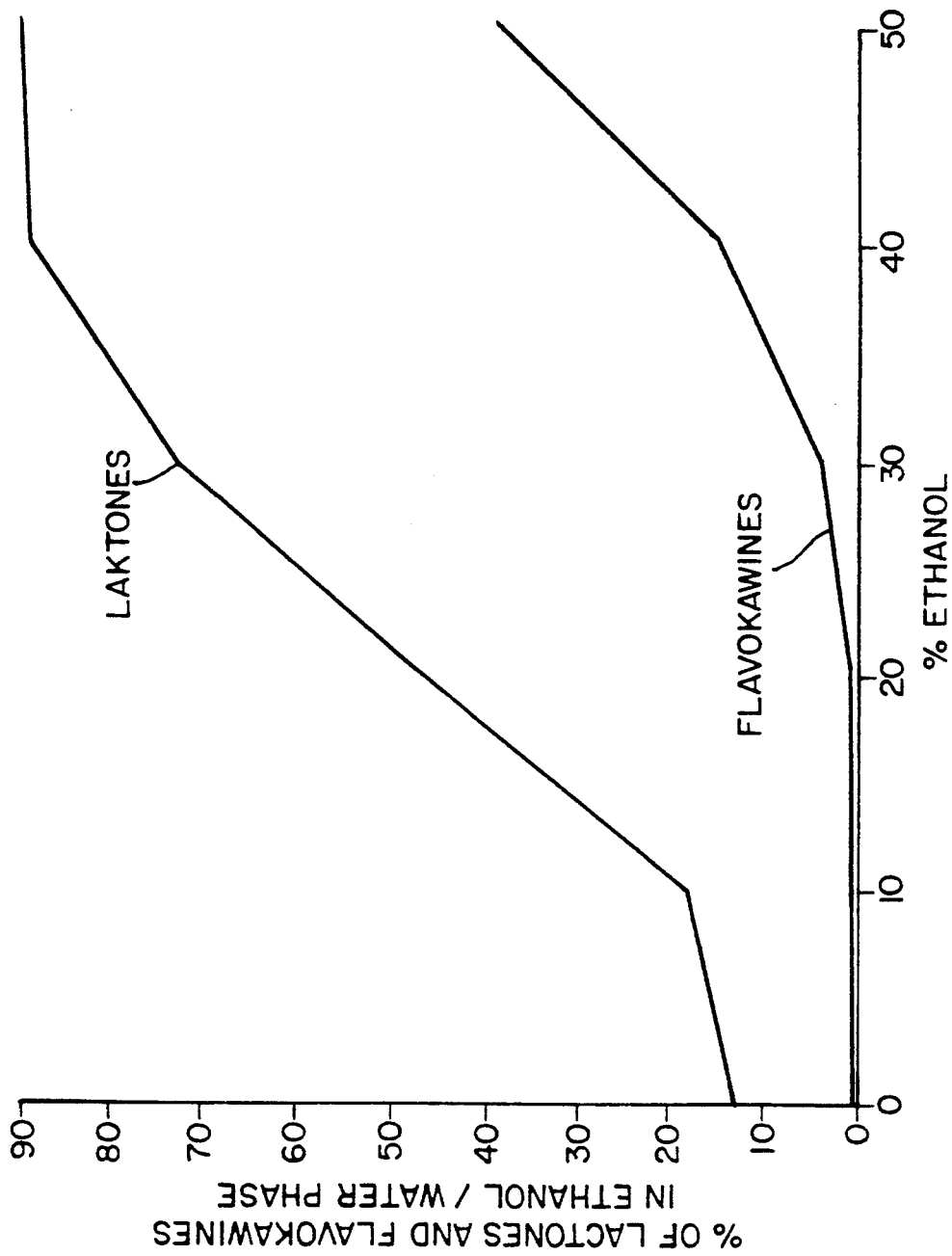

FIG. 1 depicts the proportion of compound groups in the ethylacetate/hexane phase after extraction (three times) with an equal volume of ethanol/water. FIG. 2 depicts the proportion of compound groups in the ethanol/water phase.

It can be seen from the diagrams of the substance distribution (FIGS. 1 and 2) that in particular with an ethanol content of 30 to 40% the flavokawins are depleted to less than 20% of the starting value. Under these conditions more than 70 to 80% of the kava lactones are recovered.

EXAMPLE 3 a) Extraction with chloroform 500 g kava-kava drug is reflux extracted with 10 times its amount by weight chloroform in a 6 l three-necked flask by stirring for 2 hours.

After cooling suction filtering is carried out through a large suction filter. The drug residue is extracted another 2 times in the same manner. The chloroform extract solutions are combined and concentrated to an oily consistency in a rotary evaporator at about 50° C. bath temperature.

Yield: 12.90 g kava extract with a 63% content of kava lactones b) Depletion of yellow dyes (flavokawins) by solvent distribution From the kava extract thus obtained saturated solutions in 50 ml ethanol/water mixtures in each case are prepared (about 1-2 g, each).

These batches are extracted 3 times each with the same volume of hexane or heptane. The contents of kava lactones and flavokawins are determined in the ethanol/water phase or the hexane phase. The product phase (EtOH/water) has the contents of kava lactones and flavokawins indicated in Table 2 (related to the starting extract in each case):

TABLE 2

| | | kava lactones | flavokawins |
|---|---|---|---|
| ethanol/$H_2O$ | 85:15 (v/v) | 83% | 54% |
| ethanol/$H_2O$ | 70:30 | 85% | 40% |
| ethanol/$H_2O$ | 50:50 | 73% | 8% |

It is apparent that with an ethanol content between 50 and 70% a pronounced depletion of the flavokawins occurs with an acceptable loss of kava lactones.

EXAMPLE 4

Depletion of flavokawins by distribution between acetone/water and heptane

An acetonic extract prepared according to Example 1 is concentrated to dryness and thereafter dissolved again in 55% by weight acetone/water to give a solution with 4% dry residue. This solution is extracted in a 4-stage mixer settler in counterflow with the same amount by volume of a mixture of 8 parts heptane and 2 parts acetone.

The analyses values found in the dry residue of the acetone/water phase are compared below with the starting values:

| | kava lactones | flavokawins |
|---|---|---|
| starting values (extract without heptane/acetone extraction) | 67.63% | 1.89% |
| acetone-water phase | 70.66% | 0.17% |

The invention will be further explained below with regard to the pharmacokinetic properties of the kava extracts and the pharmaceutical preparations prepared therefrom:

The bioavailabilities of kava lactones in a dog are compared with each other after administration of the extract prepared according to the invention, a commercially usual extract and a mixture of the kava lactones as pure substances.

The extract prepared according to the invention was mixed with a galenic auxiliary substance (silicon dioxide) and administered in the form of a capsule; the commercially usual extract mixed with a galenic auxiliary substance (silicon dioxide) was administered in the same manner. The mixture of the kava lactones was in equal parts, as with the extract made according to the invention, and administration was also as capsule. The dosage can be seen in Table 3.

TABLE 3

| Lactone | Extract prepared according to the invention | Mixture of the pure substances | Dosage (mg/kg) commercially prepared extract |
|---|---|---|---|
| Kawain | 1.23 | 1.23 | 1.23 |
| DH-Kawain | 1.43 | 1.43 | 1.34 |
| Methysticin | 1.14 | 1.14 | 1.25 |
| DH-Methysticin | 1.23 | 1.23 | 1.30 |
| Yangonin | 0.82 | 0.82 | 0.94 |

Blood was taken at the following times after administration: 10, 20, 40, 60, 120, 180, 240 and 360 minutes. The kava lactones were determined in the plasma by HPLC.

Figure 3:
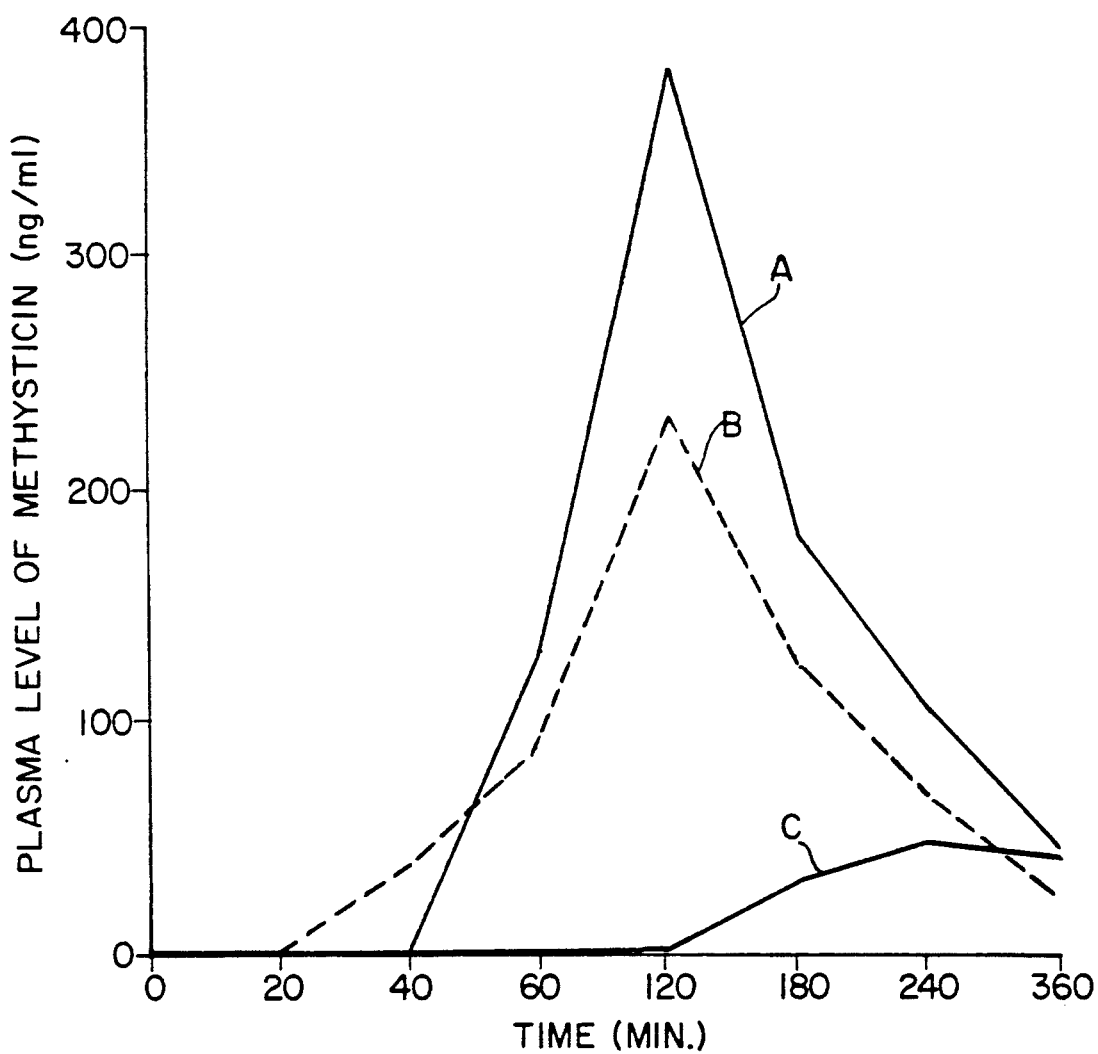
FIGS. 3 and 4 show diagrams which represent the time profile of the plamsa level of methysticin and dihydromethysticin in a dog.
Figure 4:
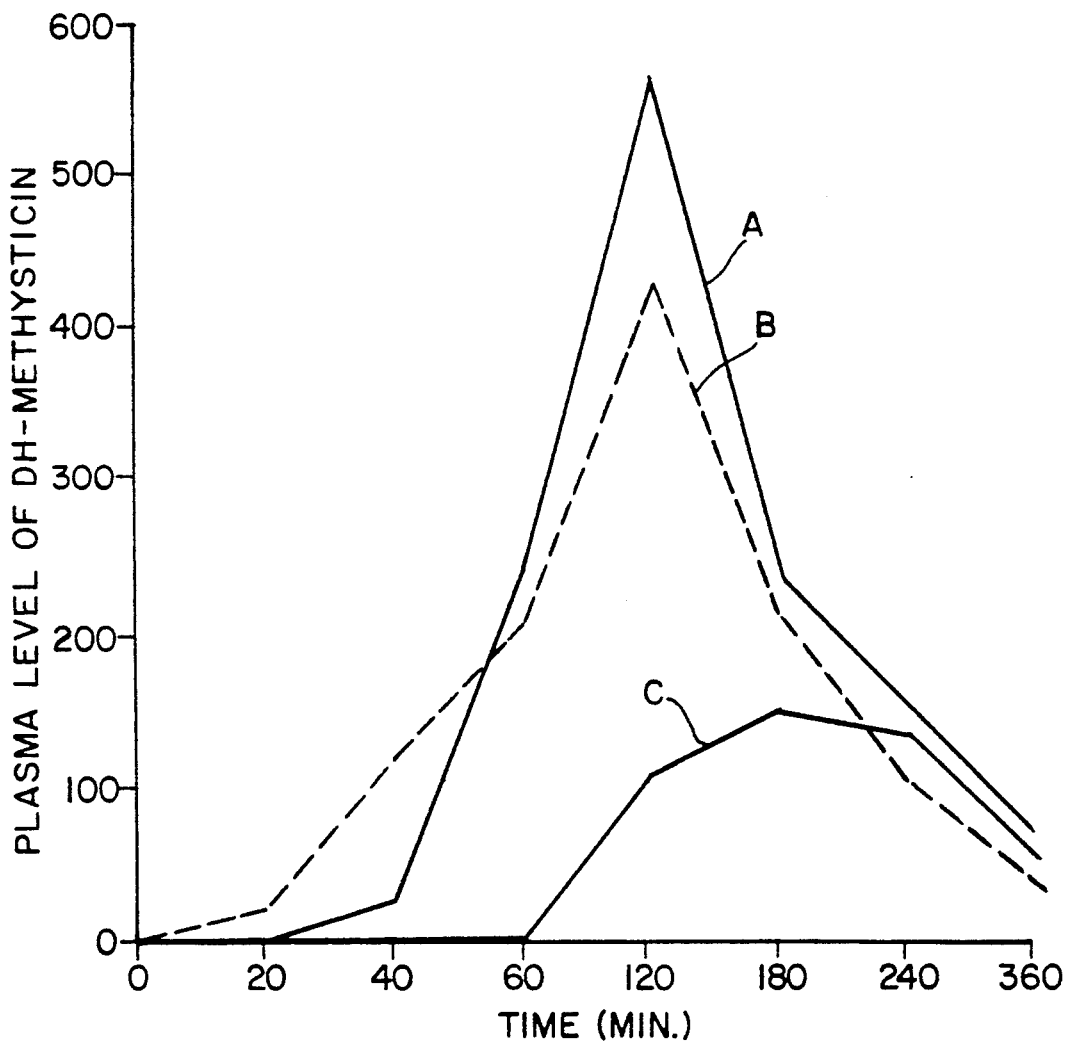

FIGS. 3 and 4 depict the plasma levels of methysticin and DH-methysticin, respectively, after administration of the extracts and the pure compounds, wherein line A is the extract produced according to the invention, line B is a commercially available extract, and line C is a mixture of the lactones".

The following AUC-values[1] (0-6 h) were found in each case in five dogs (mean values ± standard deviation) (Table 4):

TABLE 4

| Lactone | Extract made according to the invention | AUC (ng/ml · min) Mixture of the pure substances |
|---|---|---|
| Kawain | 22210 ± 5862 | — |
| DH-Kawain[2] | 4144 ± 4134 | — |
| Methysticin | 26598 ± 13956* | 4907 ± 3329 |
| DH Methysticin[2] | 58534 ± 12626** | 20686 ± 9334 |
| Yangonin | — | — |

—Plasma level below the detection limit (about 30 ng/ml lactone)
Significance level
*p < 0.05
**p < 0.01
[1]AUC = area under the curve, calculated by the trapezium rule (cf. Derendorf, Garret, "Pharmakokinetik", Wissenschaftliche Verlagsgesellschaft mbH, Stuttgart 1987
[2]DH = dihydro It was found that only the extract prepared according to the invention led to a measurable absorption of kawain and DH-kawain. The absorption of methysticin and DH-methysticin are significantly better with the extract prepared according to the invention.

In Table 5 the AUC values of four dogs are enumerated which received in crossover in each case the extract prepared according to the invention and a commercially usual extract.

TABLE 5

| Substance | | Animal extract prepared according to the invention A | AUC (ng/ml · min) commercially prepared extract* B | Quotient $AUC_A/AUC_B$ |
|---|---|---|---|---|
| Kawain | 1 | 32,080 | 30,855 | 1.04 |
| | 2 | 19,540 | 24,430 | 0.80 |
| | 3 | 22,710 | 17,325 | 1.31 |
| | 4 | 19,590 | 18,303 | 1.07 |
| DH-Kawain | 1 | 4,200 | — | — |
| | 2 | — | 3,970 | — |
| | 3 | 2,700 | 4,226 | 0.63 |
| | 4 | 11,020 | 1,153 | 9.56 |
| Methysticin | 1 | 51,070 | 30,826 | 1.66 |
| | 2 | 22,320 | 12,476 | 1.79 |
| | 3 | 21,810 | 7,620 | 2.86 |
| | 4 | 22,080 | 9,275 | 2.38 |
| DH-Methysticin | 1 | 76,480 | 58,496 | 1.31 |
| | 2 | 52,830 | 41,962 | 1.26 |
| | 3 | 63,720 | 21,762 | 2.93 |

TABLE 5-continued

| Substance | Animal extract prepared according to the invention A | AUC (ng/ml · min) commercially prepared extract* B | Quotient $AUC_A/AUC_B$ |
|---|---|---|---|
| 4 | 57,040 | 33,267 | 1.71 |

*standardized to the same dosage

A comparison was made of the relative bioavailability of the extract according to the invention and the commercially usual extract with the aid of the bioavailability quotients (quotient $AUC_A/AUC_B$). Bioequivalence is the term used when the 95% confidence interval of the bioavailability quotients lies between 0.8 and 1.20 or when ¾ of the values lie between 0.75 and 1.25 (cf. H. Blume, "Bioäquivalenz-Beurteilungsgrundlage für Generika", Pharmazeutische Zeitung 132, No. 4, pages 151-162 (1987)).

For methysticin and DH-methysticin all the bioavailability quotients are outside the range of 0.75 and 1.25 and on the average are 2.17 and 1.80 respectively. This means that the better bioavailability of the extract prepared according to the invention compared with the commercially usual extract is proved by recognized criteria. An example is the plasma levels of methysticin and DH-methysticin after administration of the different extracts or pure substances to a dog.

In the case of kawain identical absorption after administration of the two extracts is to be assumed.

In a randomized placebo-controlled double blank study the effectiveness of the extract prepared according to the invention was investigated in 40 female patients with psychovegetative and psychosomatic disturbances.

The investigation lasted a total of eight weeks. During this time, the female patients were administered either 3×1 capsules of 100 mg extract or placebo.

Figure 5:
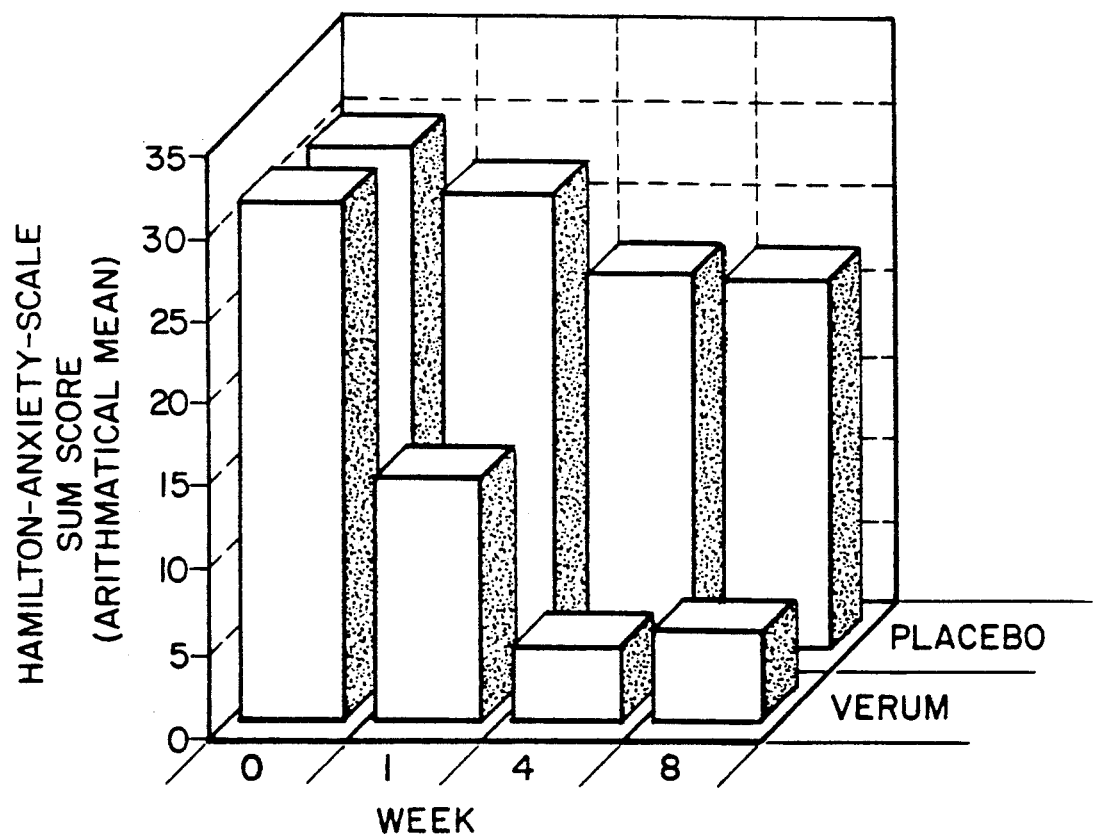
FIG. 5 is a three-dimensional representation of the Hamilton anxiety score with placebo comparison.

The efficacy was assessed with the aid of the Hamilton anxiety score (HAMA). After administration of the extract prepared according to the invention, in the fourth and eighth treatment week the HAMA score drops significantly (p<0.01 or 0.05), as apparent from the graphic illustration (FIG. 5). FIG. 5 depicts the HAMA-Score after the administration (3×100 mg) of the extract produced according to the invention and of a placebo.

I claim:

1. Dry extract from the rhizome of *Piper methysticum* Forst., wherein said extract comprises a total content of kava lactones of at least 50% by weight and a flavokawin content of at most 0.3% by weight.

2. Extract according to claim 1, comprising a total content of kava lactones of 50 to 90% by weight.

3. Extract according to claim 2, comprising a flavokawin content of less than 0.3% by weight.

4. Extract according to claim 1, comprising a total content of kava lactones of 60 to 80% by weight and a flavokawin content of less than 0.2% by weight.

5. A process for the preparation of a dry extract from the rhizome of *Piper methysticum* Forst., comprising a total content of kava lactones of at least 50% by weight and a flavokawin content of at most 0.3% by weight, comprising the steps of:
   (a) extracting the pulverized rhizome of *Piper methysticum* Forst. (rhizoma kava-kava) with a first solvent to obtain an extract solution;
   (b) concentrating said extract solution to dryness to obtain a raw extract;
   (c) dissolving said raw extract in a second solvent to obtain a raw extract solution;
   (d) depleting the content of flavokawins in said raw extract solution by either cold precipitation or solvent distribution to obtain a pure extract solution; and
   (e) concentrating said pure extract solution to dryness to obtain said dry extract having a total content of kava lactones of at least 50% by weight and a flavokawin content of at most 0.3% by weight.

6. The process according to claim 5, wherein said first solvent is chosen from the group consisting of: acetone, chloroform, ethyl acetate, low alkanols having 1 to 4 C atoms, and at least 50% by weight mixtures thereof with water.

7. The process according to claim 6, wherein said depleting step is accomplished by cold precipitation, and further wherein said cold precipitation comprising the following steps:
   (a) mixing said raw extract solution with water or an alkanol/water mixture;
   (b) cooling the mixture to 5° to 10° C.;
   (c) permitting the cooled mixture to stand for several hours, whereby a precipitate will be deposited; and
   (d) removing the precipitate from said cooled mixture to obtain said pure extract solution.

8. The process according to claim 6, wherein said depleting step is accomplished by solvent distribution, wherein said solvent distribution comprises distributing said raw extract solution between immiscible organic and aqueous phase, and separating said aqueous phase from said organic phase to obtain said pure extract solution.

9. A dry extract prepared according to the process of any one of claims 5, 6, 7 or 8.

10. A pharmaceutical preparation comprising the dry extract according to any one of claims 1, 2, or 4, and a pharmaceutically acceptable carrier.

11. Extract according to claim 1, further comprising pharmacologically inert solubilizing matrix substances, and wherein said extract has improved water solubility and bioavailability after oral administration as compared to a mixture of pure kava lactones having the same kava lactone composition.

12. Extract according to claim 11, comprising between about 10% and 50% by weight said matrix substances.

13. Extract according to claim 11, comprising about 20% by weight said matrix substances.

* * * * *